United States Patent [19]
Marquez et al.

[11] Patent Number: 5,869,666
[45] Date of Patent: Feb. 9, 1999

[54] CONFORMATIONALLY LOCKED NUCLEOSIDE ANALOGUES

[75] Inventors: Victor E. Marquez, Gaithersbury, Md.; Juan B. Rodriguez, Buenos Aires, Argentina; Marc C. Nicklaus, Elkridge, Md.; Joseph J. Barchi, Jr., Bethesda, Md.; Maqbool A. Siddiqui, Rockville, Md.

[73] Assignee: The United States of America as represented by the Secretary of the Department of Health and Human Services, Washington, D.C.

[21] Appl. No.: 818,563

[22] Filed: Mar. 14, 1997

Related U.S. Application Data

[60] Division of Ser. No. 311,425, Sep. 23, 1994, Pat. No. 5,629,454, which is a continuation-in-part of Ser. No. 126,796, Sep. 24, 1993, abandoned.

[51] Int. Cl.⁶ ..................... C07D 473/18; C07D 473/34; C07D 239/54; C07D 239/47
[52] U.S. Cl. .......................... 544/276; 544/277; 544/314; 544/317
[58] Field of Search .................................... 544/243, 244, 544/276, 277, 314, 317

[56] References Cited

U.S. PATENT DOCUMENTS 5,461,152  10/1995  Altmann et al. .................. 544/229

OTHER PUBLICATIONS

Rodriguez, J Med Chem 37, 3389 (1994).

Altmann et al. 4',6'–Methano carbocyclic thymidine: a conformationally constrained building block for oligonucleotides. Tetrahedron Letters 35(15):2331–2334 (1994).

Beard, A.R., et al. (1990) Synthesis of 2',3'–dideoxy–2',3'–α–methanocytidine. Carbohyd. Res. 205:87–91.

Codington, J.F., et al. (1962) Nucleosides. XIII. Synthesis of 3'–amino–3'–deoxy–arabinosyl–uracil via 2',3'–epxoy–lyxosyl nucleosides. J. Org. Chem. 27:163–167.

Cruickshank, K.A., et al. (1984) The benzolation of uracil and thymine. Tetrahedron Lett. 25:681–684.

Fukukawa, K., et al. (1983) Nucleosides and nucleotides. XXXXV. Facile deoxygenation of neplanocin A and nucleosides by the use of tri–n–butyltin hydride. Chem. Pharm. Bull. 31(6):1842–1847.

Jagannadh, B., et al. (1991) H NMR study of the sugar pucker of 2',3'–dideoxynucleosides with anti–human immunodeficiency virus (HIV) activity. Biochem,.Biophys. Res. Commun. 179:386–391.

Jenny, T.F., et al. (1992) Carbocyclic analogs of nucleosides. Helv. Chim. ACTA 75:1944–1954.

Jenny, T.F., et al. (1991) Carbocyclic analogs of nucleosides via modified Mitsunobu reactions. Tetrahedron Lett. 32:7029–7032.

Kim, S.K., et al. (1990) Synthesis and biological activity of ARA and 2'–deoxy–cyclopentenyl cytosine nucleoside analogues. Nucleosides and Nucleotides 9:663–677.

Kinoshita, K., et al. (1985) The structure of neplanocin C. Nucleosides & Nucleotides 4:661–668.

(List continued on next page.)

*Primary Examiner*—Mark L. Berch
*Attorney, Agent, or Firm*—Knobbe, Martens, Olson & Bear, LLP

[57] ABSTRACT

Conformationally locked 4',6'-cyclopropane-fused carboxylic nucleoside analogues. The compounds are prepared by condensing a cyclopropane-fused carbocyclic allylic alcohol with substituted purine or pyrimidine bases. The condensation products are then modified to produce the adenosine, guanosine, cytidine, thymidine, and uracil nucleoside analogues. The compounds are therapeutically useful as antimetabolites, or in the preparation of anti-metabolic agents.

16 Claims, 3 Drawing Sheets

5, B = adenine
6, B = guanine
7, B = thymine
8, B = uracil
9, B = cytosine

OTHER PUBLICATIONS

Koole, L.H., et al. (1991) Comparative structural studies of [3.1.0]–fused 2',3'–modified β–D–nucleosides by X–ray crystallography, NMR spectroscopy, and molecular mechanics calculations. J. Org. Chem. 56:6884–6892.

Marquez, V.E., et al. (1988) Total synthesis of (–)–neplanocin. A.J. Org. Chem. 53:5709–5714.

Mitsuya, H., et al. (1986) Inhibition of the in vitro infectivity and cytopathic effect of human T–lymphotrophic virus type III/lymphadenopathy–associated virus (HTLV–III/LAV) by 2'–3'–dideoxynucleosides. Proc. Natl. Acad. Sci. USA 83:1911–1915.

Taylor, E.W., et al. (1990) A stereochemical rationale for the activity of anti–HIV nucleosides. Antiviral Chem. & Chemother. 1:163–173.

Van Roey, P., et al. (1989) Correlation between preferred sugar ring conformation and activity of nucleoside analogues against human immunodeficiency virus. Proc. Natl. Acad. Sci. USA 86:3929–3933.

Van Roey, P., et al. (1990) Correlation of molecular conformation and activity of reverse transcriptase inhibitors. Ann NY Acad. Sci. 616:29–40.

Wu, J–C. and Chattopadhyaya, J. (1990) A new stereospecific synthesis of [3.1.0] bicyclic cyclopropano analog of 2',3'–dideoxyuridine. Tetrahedron Lett. 46:2587–2592.

Mitsunobu, O. (1981) The use of diethyl azodicarboxylate and triphenylphosphine in synthesis and transformation of natural products. Synthesis 1:1–28.

Molander, G.A. and Harring, L.S. (1989) Samarium–promoted cyclopropanation of allylic alcohols. J. Org. Chem. 54:3525–3532.

Molander, G.A. and Etter, J.B. (1987) Samarium–promoted, stereocontrolled cyclopropanation reactions. J. Org. Chem. 52:3942–3944.

Okabe, M. and Sun, R–C. (1989) A cyclopropano analog of 2',3'–dideoxycytidine: stereoselective formation of a [3.1.0] bicyclic system via homologous Ferrier reaction. Tetrahedron Lett. 30:2203–2206.

Plavec, J., et al. (1992) Structural analysis of 2',3'–dideoxyinosine, 2',3'–dideoxyadenosine, 2',3'–dideoxyguanosine and 2',3'–dideoxycytidine by 500–MHz H–NMR spectroscopy and ab–initio molecular orbital calculations. Biochem. Biophys. Methods 25:253–272.

Rodriguez et al. Synthesis of cyclopropane–fused dideoxycarbocyclic nucleosides structurally related to neplanocine C. Tetrahedron Letters 34(39):6233–6236 (1993).

Marquez, J Med Chem 39, 3739, 1996.

Ezzitouni, J. Chem Soc, Perkins 1, p. 1073, 1997.

5, B = adenine
6, B = guanine
7, B = thymine
8, B = uracil
9, B = cytosine

CONFORMATIONALLY LOCKED NUCLEOSIDE ANALOGUES

This application is a divisional of U.S. patent application Ser. No. 08/311,425, filed Sep. 23, 1994, U.S. Pat. No. 5,629,434 which was a continuation-in-part of U.S. patent application Ser. No. 08/126,796, filed Sep. 24, 1993 ABN.

FIELD OF THE INVENTION

This invention relates to nucleoside analogues and methods for their synthesis. More specifically, it relates to nucleoside analogues containing a cyclopropane-fused carboxylic ring.

BACKGROUND OF THE INVENTION

Nucleoside analogues, such as those species lacking the 3' hydroxyl group or both the 2' and 3' hydroxyl groups, of the naturally-occurring nucleosides can act as chain terminators of the DNA into which they are incorporated. Intense effort has focused on the design and use of these compounds as inhibitors of viral replication (Van Roey et al., (1990) *Ann. NY Acad. Sci.*, 616: 29). Although the conformation of the sugar moiety in these analogues is believed to play a critical role in modulating biological activity, including the anti-HIV 1 activity mediated by derivatives such as 3'-azido-3'-deoxythymidine (AZT) and dideoxyinosine (ddI), the main problem encountered in attempting to correlate a specific type of sugar conformation with the biological activity of nucleoside analogues is that the sugar ring is quite flexible and its conformation in solution can differ markedly from its conformation in the solid state (Jagannadh, et al., (1991) *Biochem. Biophys. Res. Commun.*, 179: 386; Plavec et al., (1992) *Biochem. Biophys. Methods*, 25: 253.). Thus, any structure-function analysis based solely on solid state conformational parameters would be inaccurate unless it was previously determined that both solution and solid-state conformations were the same.

Some [3.1.0]-fused 2',3'-modified cyclopropane-fused dideoxynucleosides (FIG. 1A; Wu and Chattopadhyaya, (1990) *Tetrahedron Lett.*, 46: 2587; Okabe and Sun, (1989) *Tetrahedron Lett.*, 30: 2203; Beard et al., (1990) *Carbohyd. Res.*, 205: 87; Codington et al., (1962) *J. Org. Chem.*, 27: 163) appear quite rigid and their altered sugar moiety shows the same conformational preference in solution as in the solid state. However, the conformation of the furanose ring in these compounds is well outside the typical range of the Northern (N) or Southern (S) geometry conformations that are characteristic of nucleosides (Koole et al., (1991) *J. Org. Chem.*, 56: 6884). A different type of [3.1.0] fusion, an epoxide ring between carbons 4' and 6', is found in the naturally-occurring carbocyclic nucleoside analogue neplanocin C (Kinoshita et al., (1985) *Nucleosides & Nucleotides*, 4: 661), which allows this compound to adopt a rigid N-geometry.

In solution there is a dynamic equilibrium between N and S type furanose conformers (Taylor et al., (1990) *Antiviral Chem. Chemother.*, 1: 163–173. The conformations of nucleosides and their analogues can be described by the geometry of the glycosyl link (syn or anti), the rotation about the exocyclic C4'–C5' bond and the puckering of the sugar ring leading to formation of the twist and envelope conformations. Two conformations are preferred for ribose ring puckering; C3'-endo (N) and C2'-endo (S). The endo and exo refer to displacement of the atom above or below the plane of the ribose ring, respectively. The torsion angles χ [C2-N1-C1'-O4' (pyrimidines) or C4-N9-C1'-O4' (purines)] and γ (C3'-C4'-C5'-O5') describe, respectively, the orientations of the base and the 5'-hydroxyl group relative to the ribose ring.

In ribonucleosides and 2'-deoxyribonucleosides, two types of sugar puckering are generally energetically preferred, namely the C3'-endo (N) and the C2'-endo (S) conformations. In DNA duplexes, a 2'-endo (S) conformation of the repeating nucleoside unit confers upon the double helix a B-conformation, whereas the 3'-endo (N) conformation induces an A-conformation double helix. The A and B forms of DNA differ in the number of base pairs per turn, the amount of rotation per base pair, the vertical rise per base pair and the helical diameter. In addition, in stretches of DNA containing the alternating purines and pyrimidines, a left-handed helix called Z-DNA may form.

Since DNA in solution may exist in several different conformations, the present invention provides a means of locking DNA into a specific conformation. This can be useful in elucidating the structural requirements influencing DNA-protein, DNA—DNA and DNA-RNA interactions and the development of valuable therapeutics able to specifically block these interactions.

SUMMARY OF THE INVENTION

The present invention provides conformationally locked compounds having the formula

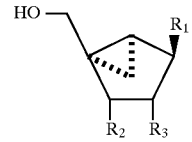

wherein $R_1$ is adenine, guanine, cytosine, thymine, uracil or a derivative thereof and $R_2$ and $R_3$ are independently H or OH. In a preferred embodiment, the compounds are locked in the Northern configuration. In various embodiments of the present invention either $R_2=R_3=H$, $R_2=OH$ and $R_3=H$ or $R_2=R_3=OH$. According to a preferred embodiment of the invention, there are provided carbocyclic-4',6'-cyclopropane-fused-2',3'-derivatives of dideoxypurines, dideoxypyrimidines, deoxypurines, deoxypyrimidines, purine ribonucleosides, and pyrimidine ribonucleosides. The invention also includes the corresponding conformationally locked nucleotides. According to another aspect of the invention there are provided oligonucleotides comprising one or more of the aforementioned compound and oligonucleotides consisting essentially of the aforementioned compounds.

According to another aspect of the invention there is provided a process for preparing the adenosine and guanosine species of the above compounds comprising providing a carbocyclic alcohol, comprising a cyclopropanated allylic alcohol, condensing the allylic alcohol with a 6-halopurine or a 2-amino-6-halopurine to form a condensation product wherein said purine derivative is linked to said allylic alcohol through a C1'N9 bond, and then displacing the halo group of the 2-amino-6-halopurine with an amino group to form an adenosine analogue or with an hydroxyl group to form a guanosine analogue. In a particular embodiment of the process, the carbocyclic alcohol is a dihydroxy cyclopropanated allylic alcohol, and the condensation product is a purine ribonucleoside analogue.

According to another aspect of the invention, there is provided a process for preparing conformationally locked pyrimidine nucleoside analogues of the invention, comprising the steps of providing a carbocyclic alcohol, comprising a cyclopropanated allylic alcohol, and condensing the carbocyclic alcohol with an N3-protected thymine or an N3 protected uracil to form a condensation product wherein the thymine or uracil derivative is linked to the carbocyclic alcohol through a C1'-N1 bond. A corresponding cytidine analogue is formed by the further steps of protecting the hydroxyl groups of a uracil analogue of the invention, prepared as described above, treating that analogue to form a triazole intermediate at C4 of uracil, and displacing the triazole group by aminolysis to form the cytidine analogue. In a particular embodiment of this aspect of the invention, the carbocyclic alcohol is a protected dihydroxycyclopropanated allylic alcohol, and the condensation product comprises a pyrimidine ribonucleoside analogue.

Deoxynucleoside analogues of the conformationally locked nucleoside analogues of the invention are prepared by a radically-induced deoxygenation of the C-2' hydroxyl function of the corresponding ribose nucleoside analogue.

The present invention also provides the compound

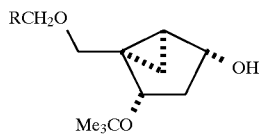

wherein R is selected from the group consisting of alkyl, aryl, alkylaryl and aroyl.

Still another embodiment of the invention is a method for preparing the above compound, comprising the steps of:

(a) providing

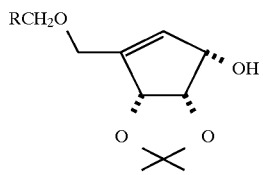

(b) reacting the compound of step (a) with trimethyl aluminum to form tert-butyloxy and hydroxy substituents at the 4' and 5' positions, respectively;

(c) protecting the hydroxy group at the 1' position by silylating the compound of step (b) with a bulky group;

(d) forming an O-(methylthio)thiocarbonyloxy group at the 5' position;

(e) removing said O-(methylthio)thiocarbonyloxy group;

(f) removing said silyl group from the 1' position to form an allylic alcohol; and (g) cyclopropanating said allylic alcohol to form a carbocyclic alcohol.

DETAILED DESCRIPTION OF THE INVENTION

Figure 1:
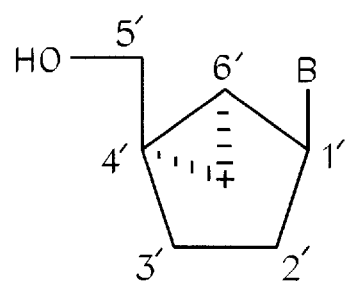
FIG. 1 shows the 4',6'-cyclopropane-fused carbocyclic dideoxynucleoside analogues according to the present invention: adenosine (5), guanosine (6), thymidine (7), uracil (8) and cytidine (9).

The compounds of the present invention represent the first examples of carbocyclic dideoxynucleosides that in solution exist locked in a defined N-geometry C3'-endo) conformation typical of conventional nucleosides. These analogues exhibit increased stability due to the cyclopropane-fused group and the substitution of carbon for oxygen in the ribose ring. The dideoxyadenosine analogue exhibits anti-HIV activity in vitro.

As used herein, the terms oligonucleoside and oligonucleoside refer to two or more contiguous nucleosides or nucleotides in 3'–5' phosphodiester linkage. In a chemical synthesis, the term "protection" refers to the addition of a chemical substituent prior to a reaction in order to prevent the group to which the substituent is attached from reacting. "Deprotection" refers to the removal of the protecting group.

This invention includes 4',6'-cyclopropane-fused carbocyclic dideoxynucleosides, 2'-deoxynucleosides and ribonucleosides as well as oligonucleotides derived from these analogues. These oligonucleotides may be synthesized exclusively from the nucleoside analogues of the present invention. In addition, oligonucleotides derived from one or more of the nucleoside analogues in combination with the naturally-occurring nucleosides are also within the scope of the present invention. These compounds comprise the five naturally-occurring nitrogenous bases adenine, guanine, cytosine, thymine and uracil. The present invention also includes methods of synthesis of these dideoxynucleoside analogues as well as the corresponding 2'-deoxyribonucleosides and ribonucleosides.

The synthetic scheme for preparing the adenosine, guanosine, cytidine, thymidine and uridine dideoxynucleoside analogues of the present invention is described in the following example. These analogues contain the naturally-occurring nitrogenous bases found in DNA and RNA in either N9 (purines) or N1 (pyrimidines) linkage to the cyclopropane-fused carbocyclic ribose ring. The synthesis and utilization of cyclopropane-fused carbocyclic nucleoside analogues containing modified bases by virtue of substitution of the purine and pyrimidine rings is also within the scope of the present invention.

The salient features of the nucleoside analogue synthetic scheme that is exemplified include a "hydroxy-directed" cyclopropanation of a 5'-OH-protected allylic alcohols 10 and 29 via a samarium (2+) carbenoid intermediate (Molander and Etter, (1987) *J. Org. Chem.* 52: 3942; Molander and Harring, (1989) *J. Org. Chem.,* 54: 3525) to generate 4',6'-cyclopropane-substituted carbocyclic alcohols 11 and 30 (Examples 1,2,21). This chemistry can be carried out analogously using 2',3',5'-OH protected carbocyclic compounds.

The 2'-deoxynucleoside analogs are prepared according to the same synthetic schemes as the dideoxynucleoside analogs, with the exception that the carbocyclic alcohol contains a tert-butyl group at the 4 position (corresponding to the 3' position in the corresponding deoxynucleoside) which protects the OH group during the reaction steps. Since this tert-butyl-substituted carbocyclic alcohol 30 is a chiral material, no optical resolution of the synthesis products is required to separate out the active isomer from a racemic mixture. The synthesis of the tert-butyl carbocyclic alcohol is briefly described below, and in detail in Examples 16–22.

(1S,4R,5S)-3-[(benzyloxy)methyl]-4,5-O-isopropylidene-2-cyclopenten-1-ol (24) is prepared from the 1-carbonyl (23) according to the procedure of Marquez et al., (J. Org. Chem., 53:5709, 1988). Although a benzyloxy group was present at position 3, the use of any 3-aryloxy, alkyloxy, alkylaryloxy or aroyloxy group for the subsequent synthetic steps is within the scope of the present invention. Compound 24 is then reacted with trimethylaluminum to form Compound 25 containing tert-butyloxy and hydroxy substituents at the 4 and 5 positions, respectively. The tert-butyl group effectively protects the 4-hydroxy group in all subsequent synthetic steps. Compound 25 is then silylated to protect the hydroxy group at the 1 position, forming compound 26. It is important that the silylating agent be a large, bulky chemical group in order to effectively repel the tert-butyl group, thus allowing the next synthetic step to proceed efficiently. Compound 26 is reacted with methyl iodide and carbon disulfide to form a (methylthio) carbonyloxy group at the 5 position (Compound 27). This bulky group is able to fit between the silyl and tert-butyl group due to repulsive forces acting between the bulky groups. The entire O-(methylthio) carbonyloxy group is then removed with tri-n-butyltin hydride to form compound 28. The silyl group is then removed with tetrabutylammonium fluoride to form the allylic alcohol 29. The allylic alcohol is then cyclopropanated as described above to form the cyclopropanated carbocyclic alcohol 30 containing a tert-butyl substituent at the 4 position which protects the hydroxy group at this position.

The purine nucleoside analogues are then prepared as described in Examples 3–10. Both carbocyclic alcohols 11 and 30 are used as starting materials for purine synthesis. The carbocyclic alcohol 11 is reacted with a 6-halo-substituted purine ring in a Mitsunobu-type condensation (Mitsunobu, (1980) *Synthesis* 1, Jenny et al., (1991) *Tetrahedron Lett.* 32: 7029; Jenny et al., (1992) *Helv. Chim. Acta.* 75: 1944) to form halogenated intermediates 13 (Example 5) and 14 (Example 6). Although 6-chloropurine and 2-amino-6-chloropurine were used, it is envisioned that other substitutions at the 6-position could be incorporated into the synthetic scheme to generate modified purine analogues. Furthermore, the use of other halogen-substituted purines is also contemplated. The substituent chlorine group is then displaced by ammonia to generate the 5'-OH protected adenosine 16 (Example 7) or displaced by benzylate to generate the 5'-OH and 6-OH protected guanosine 17 (Example 8) derivatives which are then deblocked to generate the adenosine and guanosine derivatives 5 (Example 9) and 6 (Example 10).

The main features of the pyrimidine analogue synthetic scheme are described in Examples 11–15. This scheme includes condensation of N-3 protected uracil or N-3 protected thymine with carbocyclic alcohols 11 or 30 to generate the protected Mitsunobu condensation products 18 (Example 11) and 19 (Example 12). The use of substituted N-3 protected bases is also within the scope of the present invention. Compounds 18 and 19 are then deprotected to generate the thymidine analogue 7 (Example 13) and the uracil analogue 8 (Example 14). The 5'-OH group of compound 8 is then protected with an acetyl group to generate intermediate 21 (Example 15) and the resulting compound is derivatized with a triazole group at C4 of the pyrimidine ring, although the use of a number of groups for this derivatization is contemplated. The triazole group is then displaced by ammonia to generate the cytidine derivative 9 (Example 15).

Synthesis of Conformationally Locked Ribonucleosides

The ribonucleoside species of the invention are prepared be replacing the carbocyclic allylic alcohol of Examples 3, 4, 9, and 10 with a the equivalent isopropylidene-protected carbocyclic allylic alcohol formed from D-ribose according to the procedure set forth in Marquez, V. et al. (Compound 8a in *J. Org. Chem.* (1988), 53: 5709–5714). This compound is then cyclopropanated as described in Example 1. The remainder of the synthetic steps are the same commencing with the Mitsunobu coupling reaction as described in Examples 3, 4, 9, and 10.

One of ordinary skill in the art will appreciate that there are a number of alternative ways in which to perform certain synthetic steps of the present invention using well known reactions.

The dideoxynucleoside analogue compounds of the present invention are incapable of forming oligonucleotides, DNA or RNA due to the absence of a 3' hydroxyl group necessary for chain elongation; however the ribonucleoside and deoxyribonucleoside species, having the 3'-hydroxyl present, can react to form the polynucleotides in the manner of the naturally occurring nucleoside species.

Once these 2'-deoxyribonucleoside and ribonucleoside analogues are synthesized, and phosphoramidites of the base analogues, which will react like conventional phosphoramidites, are prepared, one of ordinary skill will be able to synthesize oligodeoxyribonucleotides and oligoribonucleotides using readily available automated synthesizers by methods well known in the art (Gait, M. J. ed., Oligonucleotide Synthesis: A Practical Approach, Washington, D.C.: IRL Press, 1984). In addition, the preparation of the corresponding nucleotides containing attached phosphate groups using well known chemical methods is also within the scope of the present invention.

These 2'-deoxyribonucleoside and ribonucleoside analogues are expected to adopt a rigid N-geometry conformation in solution. The 2'-deoxyribonucleoside and ribonucleoside analogues are useful for the same purposes as are conventional nucleosides. They can be used, for example, to synthesize nucleic acid coding sequences, regulatory sequences known to interact with DNA binding proteins, and to synthesize probes for hybridization analysis. These oligonucleotide analogues can also be inserted into expression vectors from which functional sequences will be transcribed. Each analogue is thus useful in forming functional DNA or RNA oligonucleotide analogues. DNA and RNA oligonucleotides containing the 2'-deoxynuceoside and ribonucleoside analogs will exhibit increased stability and will be useful as antisense molecules for inhibiting mRNA translation for a gene of interest. Furthermore, the nucleoside analogues can be used as a scientific tool to synthesize and lock DNA into the A-conformation thus allowing subsequent discoveries.

The synthesis of 2'-deoxyribonucleoside and ribonucleoside analogues will allow the preparation of molecules which will interact more strongly with proteins and enzymes requiring Northern conformers for substrates. Since the conformation of a particular nucleic acid is an equilibrium conformation, the overall interaction of DNA and RNA binding proteins with DNA and RNA, respectively, is the sum of the interactions with the various conformations. DNA and RNA with nucleotide units locked in the N-geometry conformation will be useful in elucidating the interactions between nucleic acids and nucleic acid binding proteins. This will lead to novel therapeutics which can inhibit specific DNA-protein interactions thus inhibiting the synthesis of deleterious gene products and/or increasing the synthesis of beneficial gene products. It is also envisioned that other types of cyclopropane-fused nucleosides prepared using this technology will generate compounds locked in the opposite (S) configuration by simply changing the relative position of the base and the hydroxymethyl groups.

Compared to conventional oligonucleotides, oligonucleotides synthesized using the nucleoside analogues of the present invention will have a significantly smaller entropy change upon duplex formation due to their rigidity. This will result in a more favorable negative free energy change upon hybridization relative to conventional DNA fragments. Using these new methodology, by combining natural nucleosides with the analogues of the present invention, DNA fragments can be constructed to create a specific "bend" in the double helix which may lead to either increased or decreased binding to proteins and/or nucleic acids.

The foregoing examples are intended to be illustrative rather than limiting with the full scope of the invention being defined by the following appended claims.

All chemical reagents were obtained from commercial sources. Silica gel column chromatography was performed on silica gel 60, 230–240 mesh (Merck). Analytical thin layer chromatography (TLC) was performed on Analtech Uniplates silica gel GF. Protein and $^{13}$C-NMR spectra were recorded in a Brucker AC-250 instrument at 250 and 62.9 MHz, respectively. NMR conformational studies were performed in a Brucker AMX-500 instrument at 500 MHz. Chemical shifts are expressed as δ values with reference to tetramethylsilane. Positive-ion fast bombardment (FAB) mass spectra were obtained on a VG 7070E mass spectrometer equipped with a FAB ion source. The sample was dissolved in a glycerol matrix, and ionization was effected by a beam of xenon atoms. Elemental analyses were performed by Atlantic Microlab, Inc., Norcross, Ga. UV spectra were recorded in a Shimadzu Model UV-2101PC spectrophotometer. These values are listed after each synthetic step described below.

A convergent approach was used to incorporate the purine and pyrimidine bases onto the carbocyclic moiety in one step. Mitsunobu-type condensations with the appropriate bases were performed using the common intermediate carbocyclic alcohol, (+/−)-5-[(benzyloxy)methyl]-2-hydroxy-cis-bicyclo[3.1.0]hexane (11, Schemes 1 and 2).

The following invention is described below in detail using the following examples, but the methods described are broadly applicable for the preparation of all of the nucleoside analogues described herein and are not limited to the examples given below.

EXAMPLE 1

Synthesis of the Intermediate Carbocyclic Alcohol 1-Benzyloxymethyl-cis-bicyclo[3.1.0]hexane-4-ol 11

Samarium metal (5.04 g, 33.6 mmol) was added to a dry round-bottomed flash which was simultaneously flushed with argon and flamed dry. Anhydrous tetrahydrofuran (THF; 50 ml) was then added followed by a solution of mercuric chloride ($MgCl_2$; 0.88 g, 3.2 mmol) in 10 ml THF. The mixture was stirred for 10 min followed by addition of allylic alcohol 10 (1.52 g, 7.45 mmol). The reaction mixture was cooled to −78° C. followed by addition of chloroiodomethane ($CH_2ICl$; 2.32 ml, 32 mmol) and the mixture was stirred at −78° C. overnight. The mixture was allowed to warm to room temperature and stirred for one hour. The reaction was quenched with 300 ml saturated $Na_2CO_3$ and extracted several times with methylene chloride. The combined organic layers were washed with brine, dried over $MgSO_4$, filtered and evaporated yielding pure compound 11 as a colorless oil in nearly theoretical yield. The product was used in the next step without further purification.

FAB MS (m/z, %)=201 ({MH-$H_2O$}+,9); 91 (100); 71 (98). $^1$H-NMR ($CDCl_3$) δ=0.47 (dd, J=5.2, 8.0 Hz, 1H, H-6 exo); 0.85 (t, J=5.2 Hz, 1H, H-6 endo); 1.40 (m, 1H, H-5); 3.42 (s, 2H, H-7); 4.50 (s, 2H, $PhCH_2$—); 4.55 (m, 1H, H-4); 7.25–7.40 (m, 5H, aromatic protons). $^{13}$C-NMR ($CDCl_3$); δ=8.93 (C-6); 27.17 (C-5); 27.51 (C-3); 28.25 (C-1); 29.64 (C-2); 72.39 (C-7); 73.60 (C-4); 74.42 (C-8); 127.36 (C-3' & C-4'); 128.17 (C-2') 138.35 (C-1').

EXAMPLE 2

4-Acetoxy-1-benzyloxy-cis-bicyclo-[3.1.0]-hexane 12

A solution of compound 11 (109 mg, 0.5 mmol) in 3 ml anhydrous pyridine was treated with 2 ml acetic anhydride and the mixture was stirred overnight at room temperature. The solvent was evaporated and the residue purified by flash chromatography eluting with hexane-ethyl acetate (4:1) to yield mg of the stable acetate derivative 12.

Figure 2:
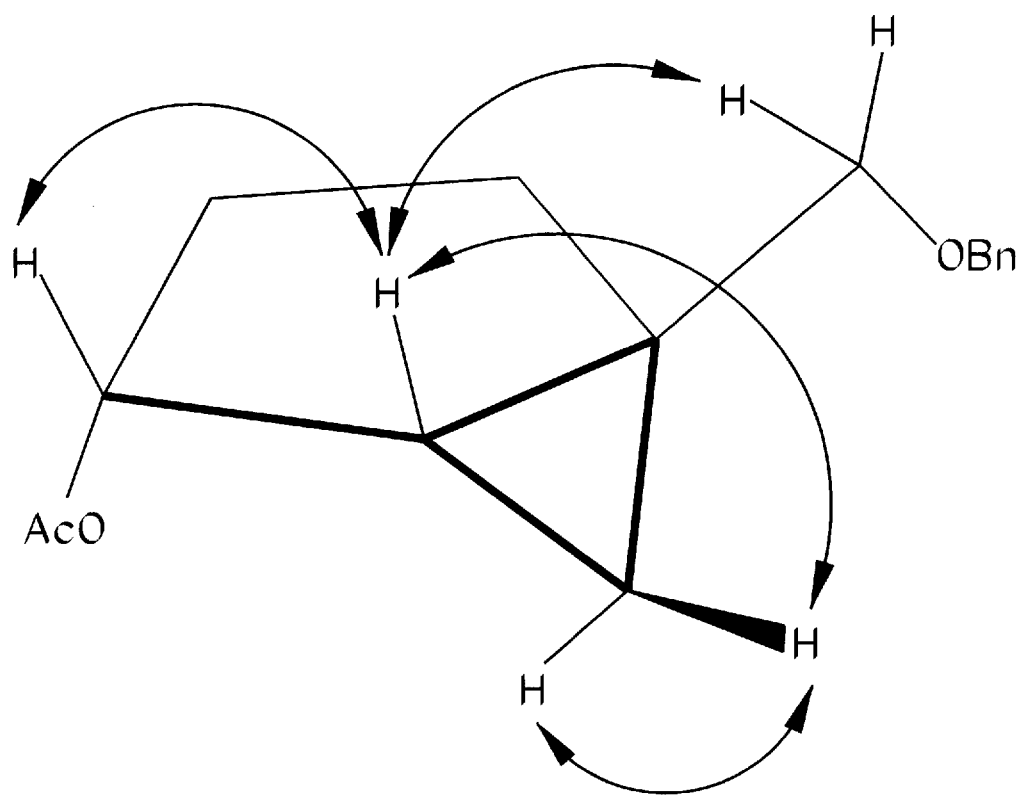
FIG. 2 shows the conformation of compound 12 as deduced by $^1$H-NMR. The double arrows represent reciprocal positive enhancements in a 1-D Nuclear Overhaeuser Effect (NOE) difference experiment.

Results from the NOE difference $^1$H-NMR spectra for the acetate 12 (FIG. 2) agreed well with the disposition of the bicyclic system as inferred by the mode of cyclopropanation.

$^1$N-NMR ($CDCl_3$); δ=0.54 (dd, J=5.4, 8.0 Hz, 1H, H-6 exo); 0.85 (t, J=5.4 Hz, 1H, H-6 endo); 1.53 (m, 1H, H-5); 2.02 (s, 3H, $COCH_3$); 3.43 (s, 2H, H-7); 4.50 (s, 2H, $PhCH_2$—); 5.30 (dt, J=4.7, 8.2 H, 1H, H-4); 7.30 (m, 5H, aromatic protons). $^{13}$C-NMR ($CDCl_3$) δ=9.99 (C-6); 21.12 ($COCH_3$); 24.49 (C-5); 26.36 (C-3); 27.05 (C-C-2); 28.50 (C-1); 72.52 (C-7); 74.19 (C-8); 76.77 (C-4); 127.41 (C-3' & C-4'); 128.23 (C-2'); 138.32 (C-1'); 171.23 (CO). Anal. Calculated for $C_{16}H_{20}O_3$=C 73.83 H 7.74. Found C 73.71, H 7.79.

Synthesis of Purine Dideoxynucleoside Analogues

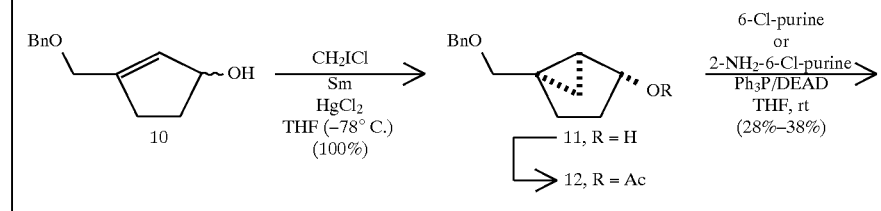

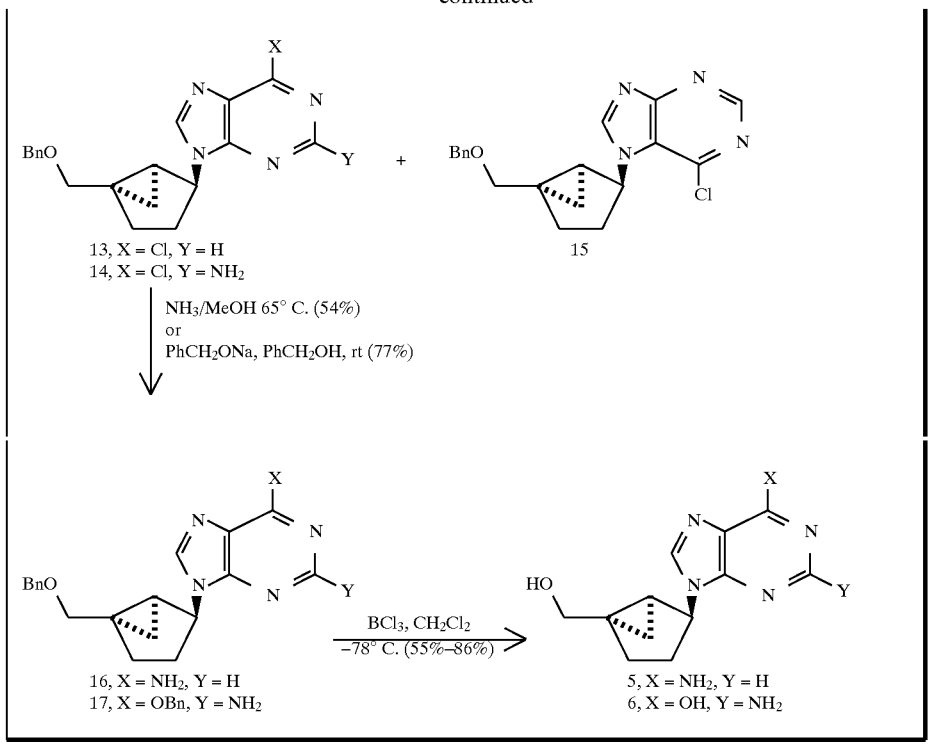

EXAMPLE 3

5'-Benzyloxy-4',6'-cyclopropyl-2',3'-dideoxy-6-chloroadenosine 13

To a suspension of 6-chloropurine (148 mg, 0.96 mmol) in 3 ml anhydrous THF was added diethylazodicarboxylate (DEAD; 206 mg, 0.96 mmol) and the resulting mixture was stirred vigorously for 10 min. Alcohol 11 was then added (218 mg, 1 mmol in 5 ml THF) and the reaction was stirred overnight at room temperature. The solvent was evaporated and the residue was adsorbed on silica gel and purified by column chromatography. The products eluted with hexane-:ethyl acetate (3:2) resulting in 75 mg (21% yield) of pure compound 13 as a white solid and 24 mg of 7-N derivative 15 as a pale yellow oil.

Compound 13, m.p.=118°–119° C. FAB MS (m/z, %)=357 (12 ), 355 (MH+, 35), 247 (11), 155 (34) 91 (100). $^1$H-NMR (CDCl$_3$) δ===0.76 (m, 2H, H-7'); 1.56 (dd, J=4.3, 8.2 Hz, 1H, H-6'); 1.65–2.00 (m, 3H, H-2' & H-3' α); 2.25 (m, 1H, H-3'β); 3.29 (d, J=9.9 Hz, 1H, H-5a'); 3.95 (d, J=9.9 Hz, 1H, H-5b'); 4.63 (s, 2H, PhH$_2$—); 5.22 (d. J=5.5 Hz, H-1'); 7.36 (m, 5H, aromatic protons); 8.74 (s, 1H, H-8); 9.00 (s, 1H, H-2). $^{13}$C-NMR (CDCl$_3$δ=12.30 (C-7'); 26.22 (C-6'); 26.28 (C-2'); 30.26 (C-3' & 4'); 56.94 (C-1'); 72.86 (C-5'); 73.20 (PhCH$_2$—); 127.49 (C-4"); 127.64 (C-3"); 128.52 (C-2"); 131.74 (C-5); 137.95 (C-1"); 144.78 (C-8); 150.65 (C-4); 151.30 (C-6); 151.51 (C-2). Anal. Calculated for C$_{19}$H$_{19}$ON$_4$Cl=C 64.38, H 5.41, N 15.82, Cl 9.87; Found C 64.43, H 5.47, N 15.82, Cl 9.80.

EXAMPLE 4

Carbocyclic-5'-benzyl-4',6'-cyclopropyl-2',3'-dideoxy-6-chloroguanine 14

To a suspension of triphenylphosphine (Ph$_3$P; 2.672 g, 10.24 mmol) and 2-amino-6-chloropurine in 60 ml anhydrous THF was added DEAD (1.76 ml, 11.26 mmol) under an argon atmosphere and the resulting yellow mixture was stirred for 10 minutes at room temperature. A solution of compound 11 (670 mg, 3.07 mmol) in 5 ml THF was added and the mixture was stirred for 18 hours at room temperature. The solvent was evaporated and the residue absorbed on silica gel and purified by column chromatography eluting with hexane-ethyl acetate to obtain 435 mg (38% yield) of compound 14 as a white solid.

m.p.=135°–137° C. UV (MeOH) FAB MS (m/z, %)=372 (15); 370 (MH+, 42); 172 (14); 170 (43); 91 (100). $^1$H-NMR (CDCl$_3$δ=0.69 (m, 2H, H-7'); 1.50 (dd, J=3.9, 8.4 Hz, 2H, H-5'); 3.30 (d, J=9.9 Hz, 1H, H5a'); 3.88 (d, J=9.9 Hz, 1H, H5b'); 4.60 (AB q. J=14.8 Hz, 2H, PhCH$_2$—); 4.95 (d, J=5.3 Hz, 1H, H-1'); 5.05 (s, 2H, —NH$_2$); 7.35 (m, 5H, aromatic protons); 8.56 (s, 1H, H-8). $^{13}$C-NMR (CDCl$_3$) δ=12.21 (C-7'); 26.29 (C-6'); 26.46 (C-2'); 30.19 (C-3')*; 30.26 (C-4')*; 56.26 (C-1'); 73.00 (C-5'); 73.17 (PhCH$_2$—); 125.54 (C-5); 127.65 (C-4"); 127.75 (C-3"); 128.51 (C-2"); 138.09 (C-1"); 141.84 (C-8); 150.99 (C-6); 153.29 (C-2); 158.76 (C-4. Anal. Calculated for C$_{19}$H$_{20}$ON$_5$Cl.⅔H$_2$O—C 59.76, H 5.63, N 18.34, Cl 9.28. Found C 59.56, H 5.46, N 18.47, Cl 9.53.

EXAMPLE 5

Carbocyclic-5'-benzyloxy-4',6'-cyclopropyl-2',3'-dideoxyadenosine 16

Compound 13 (215 mg) was treated with 5 ml of a saturated solution of ammonia in methanol in a sealed tube and stirred at 70° C. overnight. The mixture was cooled to room temperature and the solvent was evaporated. The residue was purified by column chromatography on silica gel and eluted with CHCl$_3$-isopropanol (9:1) yielding 109 mg (54% yield) of pure compound 16 as a white solid.

m.p.=170° C. $^1$H-NMR (CD$_3$OD) δ=0.76 (m, 2H, H-7'); 1.59 (t, J=6 Hz, 1H, H-6'); 1.65–2.00 (m, 3H, H-2' & H-3'α); 2.20 (m, 1H, H-3'β); 3.40 (d, J=10.0 Hz, 1H, H5a'); 3.97 (d, J=10.0 Hz, 1H, H5b'); 4.57 (s, 2H, PhCH$_2$—); 5.02 (d, J =5.7 Hz, 1H, H-1'); 7.2–7.4 (m, 5H, aromatic protons); 8.18 (s, 1H, H-8); 8.60 (s, 1H, H-2). $^{13}$C-NMR (CD$_3$OD) δ=12.72 (C-7'); 27.27 (C-6'); 27.54 (C-2'); 31.12 (C-3'); 31.36 (C-4'); 57.96 (C-1'); 74.23 (C-5'); 74.80 (PhCH$_2$—); 120.06 (C-5); 128.64 (C-4"); 128.70 (C-3"); 129.50 (C-2"); 139.80 (C-1"); 141.08 (C-8); 149.99 (C-4); 153.50 (C-2); 157.27 (C-6). Anal. Calculated for C$_{19}$H$_{21}$ON$_5$=C 68.04, H 6.31, N 20.88; Found C 67.86, H 6.34, N 20.80.

EXAMPLE 6

Carbocyclic-5'-benzyl-4',6'-cyclopropyl-2',3'-dideoxy-6-benzylguanidine 17

Anhydrous benzyl alcohol (PhCH$_2$OH) was treated with 100 mg sodium and the suspension was vigorously stirred under an argon atmosphere until no sodium metal remained. Compound 14 was treated with 1.5 ml sodium benzylate and stirred for 10 min. The reaction was quenched with 25 ml water followed by the addition of 30 ml methylene chloride. The organic layer was washed with water until pH=7, dried with MgSO$_4$ and evaporated. The residue was purified by flash chromatography eluting with hexane-ethyl acetate (1:1) to yield 161 mg (77% yield) of pure compound 17 as a white solid.

m.p.=171° C. FAB MS (m/z, %)=442 (MH+, 49), 242 (34), 91 (100). $^1$H-NMR (CDCl$_3$δ=0.66 (m, 2H, H-7'); 1.49 (dd, J=3.8 8.4 Hz, 1H, H-6'); 3.36 (d, J=9.9 Hz, 1H, H-5a'); 3.82 (d, J=9.9 Hz, 1H, H-5a'); 4.58 (AB q. J=14.0 Hz, 1H, PhCH$_2$— at 0–5'); 4.84 (s, 2H, —NH$_2$); 4.93 (d, J=5.2 Hz, 1H, H-1'); 5.58 (AB q, J=14.8 Hz, 2H, PhCH$_2$— at C-6); 7.26–7.54 (m. 10H, aromatic protons); 8.24 (s. 1H, H-8); $^{13}$C-NMR (CDCl$_3$) δ=12.16 (C-7'); 26.47 (C-2'); 26.70 (C-6'); 30.26 (C-3' & C-4'); 55.78 (C-1'); 67.91 (PhCH$_2$— at C-6); 73.09 (C-5); 73.23 (PhCH$_2$— at 0–5'); 115.69 (c-5); 127.56, 127.63 (C-4"); 127.45, 128.18 (C-3"); 128.30, 128.45 (C-2"); 136.61 ((C-8); 138.21, 138.63 (C-1"); 153.65 (C-6); 158.90 (C-2); 1'60.90 (C-4). Anal. Calculated for C$_{26}$H$_{27}$ON$_2$N$_5$=C 70.73, H 6.16, N 15.86. Found C 70.72, H 6.21, N 15.83.

EXAMPLE 7

Carbocyclic-4',6'-cyclopropyl-2',3'-dideoxyadenosine 5

Palladium on 10% charcoal (300 mg) was purged with argon for 15 min followed by addition of 50 mg compound 16 dissolved in 5 ml methanol. The resulting mixture was treated with 1 g ammonium formate and refluxed for 3 hours. The mixture was allowed to cool to room temperature, filtered and the solvent was evaporated. The residue was purified using a reverse phase column eluted with water to yield 12 mg (33% yield) of pure compound 5 as a pale yellow solid.

m.p.=251° C. (d). UV (MeOH) λ$_{max}$260.7 (ε 15200). FAB MS (m/z, %)=338 ({MH+glycerine}+, 12), 246(MH+, 100), 136 (84), 500 MHz $^1$H-NMR (DMSO-d$_6$) δ=0.66 (m, 2H, H-7'); 1.48 (dd, J=3.9, 8.3 Hz, 1H, H-6'); 1.58 (dd, J=8.2, 14.3 Hz, 1H, H-3'α); 1.67 (dd, J=8.0, 12.5 Hz, 1H, H-2'β); 1.84 (m, 1H, H-2'α); 2.07 (dt, J=8.0, 12.0 Hz, 1H, H-3'β); 3.37 (dd, J=11.4 Hz, J=5.1 Hz, 1H, H-5a'); 3.86 (dd, J=11.4 Hz, J=5.1 Hz, 1H, H-5b'); 4.90 (d, J=6.0 Hz, 1H, H-1'); 4.99 (t, J=5.2 Hz, 1H, –OH); 7.17 (s, 2H, —NH$_2$); 8.11 (s, 1H, H-8); 8.37 (s, 1H, H-2). $^{13}$C-NMR (CD$_3$OD-D$_2$O) δ=12.51 (C-7'); 26.88 (C-6'); 27.11 (C-2'); 30.95 (C-3'); 32.99 (C-4'); 58.34 (C-1'); 66.21 (C-5'); 119.84 (C-5); 141.05 (C-8); 149.57 (C-4); 153.25 (C-2); 156.84 (C-6). Anal. Calculated for C$_{12}$H$_{15}$ON$_5$=C 58.76, H 6.16, N 28.55; Found C 58.63, H 6.19, N 28.52.

EXAMPLE 8

Carbocyclic-4',6'-cyclopropyl-2',3'-dideoxyguanosine 6

A solution of compound 17 (154 mg, 0.35 mmol) in 35 ml anhydrous methylene chloride was cooled at −78° C. under an argon atmosphere, treated with 3.0 ml 1.0M boron trichloride (BCl$_3$) and stirred for 6 hours at −78° C. The solvent was evaporated and the residue dissolved in 30 ml CH$_2$Cl$_2$. The organic layer was washed with saturated NaHCO$_3$ (3×30 ml) and water (2×30 ml), dried with MgSO$_4$ and evaporated. The residue was purified using a reverse phase column eluted with water to yield 50 mg (55% yield) of pure compound 6 as a white solid.

m.p.>300° C. UV (MeOH) λ$_{max}$254.4 (ε 10500). FAB MS (m/z, %)=354 ({MH+glycerin}+, 14), 262 (MH+, 100), 152 (66). $^1$H-NMR (DMSO-d$_6$) δ=0.60 (m, 1H, H-7' exo); 0.84 (m, 1H, H-7' endo); 1.40 (dd, J=3.7, 8.1 Hz, H-6'); 3.81 (dd, J=5.2, 10.4 Hz, H-5a'); 4.13 (dd, J=5.2, 10.4 Hz, 1H, H-5b'); 4.64 (d, J=5.8 Hz, 1H, H-1); 4.95 (t, J=5.2 Hz, 1H, —OH); 6.60 (s, 2H, —NH$_2$); 7.94 (s, 1H, H-8); 10.66 (s, 1H, H-1). $^{13}$C-NMR (DMSO-d$_6$) δ=11.03 (C-7'); 25.50 (C-2'); 25.87 (C-6'); 29.73 (C-4'); 31.89 (C-3'); 55.31 (C-1'); 63.80 (C-5'); 116.52 (C-5); 135.19 (C-8); 150.44 (C-6); 153.53 (C-2); 56.79 (C-4). Anal. Calculated for C$_{12}$H$_{15}$O$_2$N$_5$·½H$_2$O=C 54.54, H 5.85, N 26.50; Found C 54.5II.

The pyrimidine derivatives were also synthesized under Mitsunobu conditions in comparable yields using protected N-3-benzoyl thymine or N-3-benozyl uracil (Cruickshank et al., (1984) s. *Tetrahedron Lett.*, 681) as described in the following examples 9–13.

Synthesis of Pyrimidine Dideoxynucleoside Analogues

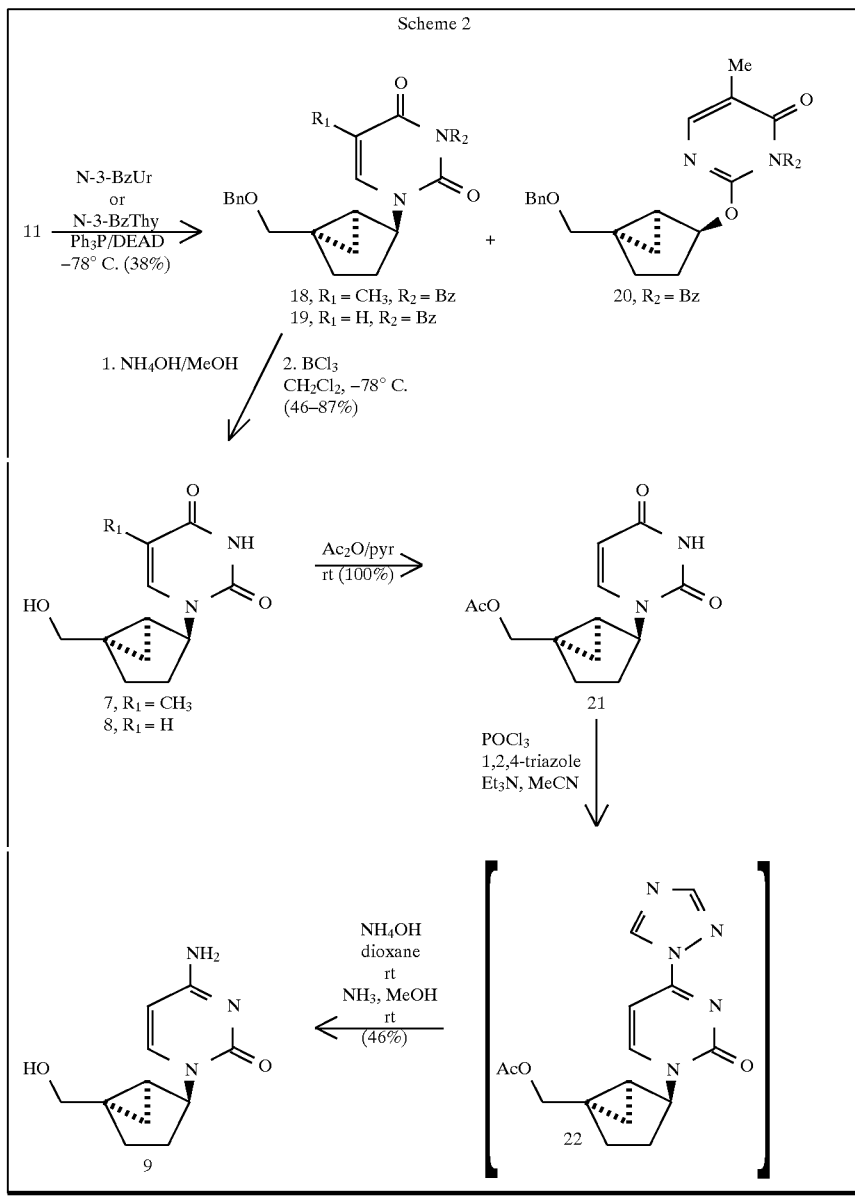

EXAMPLE 9

Carbocyclic-5'-benzoyloxy-4',6'-cyclopropyl-2',3'-dideoxy-3-benozylthymidine 18

To a solution of triphenylphosphine ($Ph_3P$; 1.340 g, 5.10 mmol) in 16 ml anhydrous THF was added DEAD (860 μl, 5.0 mmol). The mixture was stirred for 30 min at 0° C. then cooled to 45° C. To this suspension was added a solution of 3-N-benozylthymine (N-3-BzThy; 920 mg, 4 mmol) and carbocyclic alcohol 11 (460 mg, 2.10 mmol) in 16 ml THF over 45 min and the mixture was stirred overnight at 45° C. The mixture was warmed to room temperature and the solvent was evaporated. The residue was purified by flash chromatography, eluting with hexane-ethyl acetate (7:3) yielding a mixture of N-alkylation and O-alkylation products. This mixture was repurified by silica gel column chromatography, eluting with $CH_2Cl_2$-ether (97.5:2.5) to yield 330 mg (36% yield) of the desired N-alkylation product 18 as a white solid and 400 mg (44% yield) of the undesired O-alkylation product 20 as an oil. In this solvent system, compound 18 eluted faster than compound 20.

m.p.=182–184° C. FAB MS (m/z, %)=431 (MH+, 30), 323 (6), 231 (13), 105 (100), 91 (79). $^1$H-NMR ($CDCl_3$) δ=0.58 (m, 1H, H-7' exo); 0.71 (m, 1H, H-7' endo); 1.32 (dd, J=3.7, 8.8 Hz, 1H, H-6'); 1.55 (d, J=0.8 Hz, 3H, Me at C-5); 1.60–1.90 (m, 3H, H-2' & H-3'α); 2.25 (m, 1H, H-3'β); 3.26 (d, J =9.9 Hz, 1H, H-5a'(; 4.05 (d, J=9.9 Hz, 1H, H-5b'); 4.57 (AB q, J=16.5H, 2H, $PhCH_2$—); 4.98 (d, J=5.8 Hz, 1H, H-1'); 7.35 (m, 5H, benzylic protons); 7.50 (t, J=7.4 Hz, 2H, H-2'''); 7.62 (t, J=7.4 Hz, 1H, H-4'''); 7.91 (d, J=7.4 Hz, 2H, H-2'''); 8.00 (d. J=0.8 Hz, 1H, H-6). $^{13}$C-NMR ($CDCl_3$) δ=11.77 (Me at C-5); 12.18 (C-7'); 25.71 (C-2'); 26.31 (C-6'); 30.34 (C-3'); 31.02 (C-4'); 57.48 (C-1'); 73.53 (C-5') *; 73.65 ($PhCH_2$—)*; 110.25 (C-5); 127.99 (C-2'''); 128.53 (C-3'', C-4'' & C-3'''); 129.00 (C-2''); 130.37 (C-4'''); 134.73 (C-1'''); 137.90 (C-6); 138.19 (C-1''); 149.95 (C-2); 162.90 (C-4); 169.46 (C=O). Anal. Calculated for $C_{26}H_{26}O_4N_2 \cdot 1/10\ CH_2Cl_2$=71.41, H 6.02, N 6.38. Found C 72.46, H 5.98, N 6.39.

EXAMPLE 10

Carbocyclic-5'-benzoyloxy-4',6'-cyclopropyl-2',3'-dideoxy-3-benozyluridine 19

To a solution of $Ph_3P$ (857 mg, 3.26 mmol) in 10 ml anhydrous THF was added DEAD (0.500 ml, 3.2 mmol). The mixture was stirred at 0° C. for 30 min and cooled to −78° C. A suspension of 3-N-benzoyluracil (N-3-BzUr; 550 mg, 2.56 mmol) and carbocyclic alcohol 11 (280 mg, 1.27 mmol) in 25 ml THF was added to the reaction mixture over 10 min. The mixture was stirred overnight at 50° C., allowed to warm to room temperature and the solvent evaporated. The residue was purified by column chromatography (silica gel) using $CH_2Cl_2$-ether (98:2) as eluent to yield 150 mg (28% yield) of pure compound 19 as a colorless oil.

FAB MS (m/z, %)=417 (MH+, 48), 309 (9), 217 (9), 105 (100), 91 (76). $^1$H-NMR (CDCl$_3$) δ=0.61 (dd, J=3.5, 5.7 Hz 1H, H-7' exo); 0.74 (dd, J=5.7, 8.5 Hz 1H, H-7' endo); 1.31 (dd, J=3.5, 8.5 Hz, 1H, H-6'); 1.60–1.90 (m, 3H, H-2' & H-3'α); 2.20 (m, 1H, H-3'β); 3.28 (d, J=9.9 Hz, 1H, H-5a'); 4.07 (d, J=9.9 Hz, 1H, H-5b'); 4.51 (AB q, J=16.5 Hz, 2H, PhCH$_2$—); 4.95 (d, J=5.4 Hz, 1H, H-1'); 5.42 (d, J=8.1 Hz, 1H, H-5__; 7.30–7.40 (m, 5H, benzylic protons); 7.47 (t, J=7.4 Hz, 2H, H-3'''); 7.62 (dt, J=7.4, 1.0 Hz, 1H, H-4'''); 7.92 (dt, J=7.4, 1.0 Hz, 1H, H-2'''); 8.26 (d. J=8.1 Hz, 1H, H-6). $^{13}$C-NMR (CDCl$_3$) δ=12.25 (C-7'); 25.29 (C-2'); 26.18 (C-6'); 30.22 (C-3'); 30.98 (C-4'); 57.83 (C-1'); 73.28 (C-5')*; 73.59 (PhCH$_2$—)*; 101.35 (C-5); 127.45 (C-4"); 127.88 (C-3)*; 128.44 (C-2")*; 128.98 (C-2''')*; 130.30 (C-3'''); 131.55 (C-4'''); 134.80 (C-1'''); 137.95 (C-1''); 142.45 (C-6); 149.88 (C-2); 162.14 (C-4); 169.14 (CO). Anal. Calculated for $C_{25}H_{24}O_4N_2$=C 72.10, H 5.81, N 6.73. Found C 71.84, H 5.89, N 6.59.

EXAMPLE 11

Carbocyclic-4',6'-cyclopropyl-2',3'-dideoxythymidine 7

Compound 18 (150 mg, 0.35 mmol) was suspended in 100 ml methanol. Concentrated ammonia (4 ml) was then added and the mixture was stirred at room temperature for 16 hours. The solvent was evaporated and the residue was dissolved in 30 ml $CH_2Cl_2$. The organic layer was washed with saturated NaHCO$_3$ (3×30 ml) and water (2×30 ml), dried with MgSO$_4$ and evaporated. The residue was purified by flash chromatography (silica gel) using $CH_2Cl_2$-isopropanol (97:3) as eluent to obtain 105 mg (92% yield) of the N-3 deblocked intermediate as a white solid.

A solution of the N-3 deblocked intermediate (85 mg in 20 ml anhydrous (CH$_2$Cl$_2$) cooled to −78° C. under argon was treated with BCl$_3$ (1.0M in hexane, 1.80 ml) and stirred for 6 hours at −78° C. Methanol (4.0 ml) was added at the same temperature and the mixture was allowed to warm to room temperature. The solvent was evaporated and 4 ml methanol was again added followed by evaporation of the solvent. This procedure was repeated 6 times. The residue was purified by C-18 reverse phase chromatography eluting with water to yield 28 mg (46% yield) of pure compound 7 as a white solid.

m.p.=205–207° C. $^1$H-NMR (CDCl$_3$) δ=0.57 (dd, J=4.0, 5.6 Hz, 1H, H-7' exo); 0.68 (dd, J=5.6, 7.8 Hz, 1H, H--7' endo); 1.27 (dd, J=4.0, 7.7 Hz, 1H, H-6'); 1.54 (d, J=1.0 Hz, 3H, Me at C-6); 1.65–1.90 (m, 3H, H-2' & H-3'α); 2.20 (m, 1H, H-3'β); 3.34 (d, J=9.9 Hz, 1H, H-5a'); 4.01 (d, J =9.9 Hz, 1H, H-5b'); 4.55 (AB q. J=16.5 Hz, 2H, PhCH$_2$—); 4.98 (d, J=6.1 Hz, 1H, H-1'); 7.34 (m, 5H, aromatic protons), 7.88 (d, J=1.0 Hz, 1H, H-6); 8.15 (s, 1H, NH). $^{13}$C-NMR 9CDCl$_3$) δ=11.78 (Me at C-5); 12.14 (C-7'); 25.78 (C-2'); 26.34 (C-6'); 30.25 (C-3'); 30.96 (C-4'); 57.16 (C-1'); 73.47 (C-5') *; 73.63 (PhCH$_2$—)*; 110.22 (C-5); 127.92 (C-4"); 128.50 (C-3"); 128.56 (C-2"); 137.94 (C-6); 138.39 (C-1"); 151.01 (C-2). Anal. Calculated for $C_{19}H_{22}O_3N_2$—C69.92, H 6.79, N 8.58. Found C 69.78, H 6.85, N 8.53.

EXAMPLE 12

Carbocyclic-4',6'-cyclopropyl-2',3'-dideoxyuridine 8

A solution of compound 19 (120 mg, 0.29 mmol) in 60 ml methanol was treated with concentrated ammonia and the mixture was stirred for 16 hours at room temperature. The solvent was evaporated and the residue was purified by flash chromatography eluting with $CH_2Cl_2$-isopropanol (97:3) to obtain 77 mg (86% yield) of the N-3 deblocked intermediate as a white solid.

A solution of this N-3 deblocked intermediate (67 mg, 0.21 mmol) in 16 ml anhydrous $CH_2Cl_2$ was cooled at −78° C. under argon was treated with 1.50 ml 1.0M BCl$_3$ in hexane and stirred for 6 hours at −78° C. The reaction was quenched as described for compound 7. The residue was purified by flash chromatography using $CH_3Cl_2$-isopropanol (9:1) as solvent to yield 41 mg (87% yield) of pure compound 8 as a white solid.

m.p.=154°–156° C. $^1$H-NMR (CDCl$_3$) δ=0.59 (dd, J=3.8, 5.7 Hz, 1H, H-7' exo); 0.72 (dd, J=5.7, 8.7 Hz, 1H, H-7' endo); 1.26 (dd, J=3.8, 8.7 Hz, 1H, H-6'); 1.55–1.90 (m, 3H, H-2' & H-3'α); 2.15 (m, 1H, H-3'β); 3.27 (d, J=9.9 Hz, 1H, H-5a'); 4.40 (d, J =9.9 Hz, 1H, H-5b'); 4.52 q. J=16.4 Hz, 2H, PhCH$_2$—); 5.00 (d, J=5.8 Hz, 1H, H-1'); 5.37 (dd, J=1.4, 8.0 Hz, 1H, H-5); 8.11 (d, J=8.0 Hz, 1H, H-6); 9.90 (d, J=1.4 Hz, 1H, —NH); $^{13}$C-NMR (CDCl$_3$) δ=12.19 (C-7'); 25.42 (C-2'); 26.24 (C-6'); 30.16 (C-3'); 30.92 (C-4'); 57.35 (C-1'); 73.25 (C-5')*; 73.62 (PhCH$_2$—)*; 101.59 (C-5); 127.39 (C-4"); 127.83 (C-3"); 128.42 (C-2"); 137.96 (C-1"); 142.58 (C-6); 151.21 (C-2); 163.74 (C-4). Anal. Calculated for $C_{18}H_{20}O_3N_2$—c 69.21, h 6.45, n 8.97. Found C 69.13, H 6.44, N 9.02.

EXAMPLE 13

Carbocyclic-4',6'-cyclopropyl-2',3'-dideoxycytidine 9

Compound 8 (120 mg, 0.54 mmol) was dissolved in 3 ml anhydrous pyridine, treated with 2 ml acetic anhydride and stirred overnight. Evaporation of the solvent produced the 5'-monoacetyl derivative 21 in almost theoretical yield. This compound was used in the next step without further purification.

Triethylamine 9Et$_3$N; 540 µl, 3.88 mmol) was added to a mixture of 1,2,4-triazole (280 mg, 4.05 mmol), phosphorous oxychloride (POCl$_3$; 81 µl, 0.867 mmol) and anhydrous acetonitrile (2.3 ml) under argon. Compound 21 (100 mg, 0.45 mmol) in 2.0 ml acetonitrile was then added and the reaction mixture was stirred at room temperature for 24 hours. Et$_3$N (375 µl, 2.67 mmol) and water (97 µl) were then added, the mixture was stirred for 10 min and then solvent was evaporated. The residue was partitioned between CH$_2$Cl$_2$ (50 ml) and saturated NaHCO$_3$ (50 ml). The organic layer was removed and the aqueous layer was extracted with CH$_2$Cl$_2$ (2×50 ml). The combined organic layers were dried with MgSO$_4$ and the solvent evaporated to obtain compound 22 which was used in the next step without purification.

The residue was dissolved in 10 mo dioxane, treated with 1.6 ml aqueous ammonia and stirred overnight. The solvent was evaporated and the residue was treated with methanolic ammonia (saturated at −70° C. and stirred for 20 hours at room temperature. The solvent was evaporated and the residue purified by preparative TLC using $CH_2Cl_2$-isopropanol-$Et_3N$ (70:30:1) as eluent to obtain 31 mg (37% yield) of pure compound 9 as a white solid.

m.p.=222–224° C. UV (MeOH) $\lambda_{max}$ 276.5 (ε 8400). FAB MS (m/z, %)=314 ({MH+glycerine}+,9): 222 (MH+, 90); 152 (7); 112 (100. $^1$N-NMR (DMSOd$_6$) δ−0.50 (dd, J=3.7, 5.1 Hz, 1H, H-7' exo); 0.60 (dd, J=5.1, 8.6 Hz, 1H, H-7' endo); 1.15 (dd, J=3.7, 8.6 Hz, 1H, H-6'); 3.32 (dd, J=5.0, 11.4 Hz, 1H, H-5a'); 3.78 (dd, J=5.0, 11.4 Hz, 1H, H-5b'); 4.77 (d, J=6.3 Hz, 1H, H-1'); 4.89 (t, J=5.0 Hz, 1H, —OH); 5.67 (d, J=7.3 Hz, 1H, H-5); 7.08 (broad, 2H, —$NH_2$); 7.86 (d, J =7.3 Hz, 1H, H-6). $^{13}$C-NMR (DMSOd$_6$) δ=11.07 (C-7'); 24.85 (C-2'); 25.75 (C-6'); 29.70 (C-3'), 32.51 (C-4'); 57.11 (C-1'); 63.78 (C-5'); 92.99 (C-5); 142.72 (C-6); 154.88 (C-2); 164.59 (C-4).d Anal. Calculated for $C_{11}H_{15}O_3N_2 \cdot \frac{1}{3}H_2O$—C 58.14, H 6.95, N 18.49. Found C 58.14, H 6.88, N 18.41.

EXAMPLE 14

Conformational analysis of dideoxynucleoside analogues

With the exception of signals corresponding to the individual aglycons, the $^1$H NMR spectra of compounds 5–9 were nearly identical and no apparent changes in the coupling constants were observed between 25° C. and 80° C. This indicated that these compounds had a highly similar rigid conformation in solution. Using compound 5 as a prototype, the pseudoanomeric signal appeared as a doublet with a coupling constant of 6.0 Hz centered at δ=4.90. To understand the multiplicity of this signal, models of N- and S-conformers of 5 were constructed using the QUANTA program version 3.2.4 using CHARMm version 21 with the standard parameter set. The structures were minimized by systematic conformational search and the implicated torsion angles were measured for both conformers. For the N-conformer the values were: H6'-C6'-C1'-H1' (−86.1°), H1'-C1'-C2'-H2'β (91.3°) and H1'-C1'-C2'-H2'α (−23.9°).

Although the Karplus equation, defined as an empirically-derived correlation between the coupling constant J for the H/H interaction in a H-C1-C2-H system and the dihedral angle (θ) formed between the planes that contain H-C1-C2 and C1-C2-H, may not apply perfectly due to the distortion produced by the fused cyclopropane ring, the torsion angle values measured for the N-conformer suggest that two of the three coupling constants should be very close to zero. Conversely, none of the same torsion angles measured for the S-conformer approached 90° (−134.7°, 175.7° C. and 60.9°). Thus, the torsion angles measured for the N-geometry agree better with the multiplicity observed for the pseudoanomeric signal of 5 (doublet, J=6 Hz), in the $^1$H NMR spectrum. These torsion angles are also similar to those measured from the crystal structure of neplanocin C, suggesting that structures 5–9 have equivalent N-geometries in solution. The N-geometry in compounds 5–9 can only be achieved if the bicyclo[3.1.0]hexane system exists as a pseudoboat, since a pseudochair conformation would correspond to the S-geometry. A search for compounds containing unrestricted bicyclo[3.1.0]hexanes in the Cambridge Structural Data Base (Allen, et al., (1979) *Acta. Crystallogr.*, B35, 2331) revealed that in the seven examples found the pseudoboat was the only form of puckering observed.

EXAMPLE 15

Evaluation of anti-HIV activity of dideoxynucleosides

Figure 3:
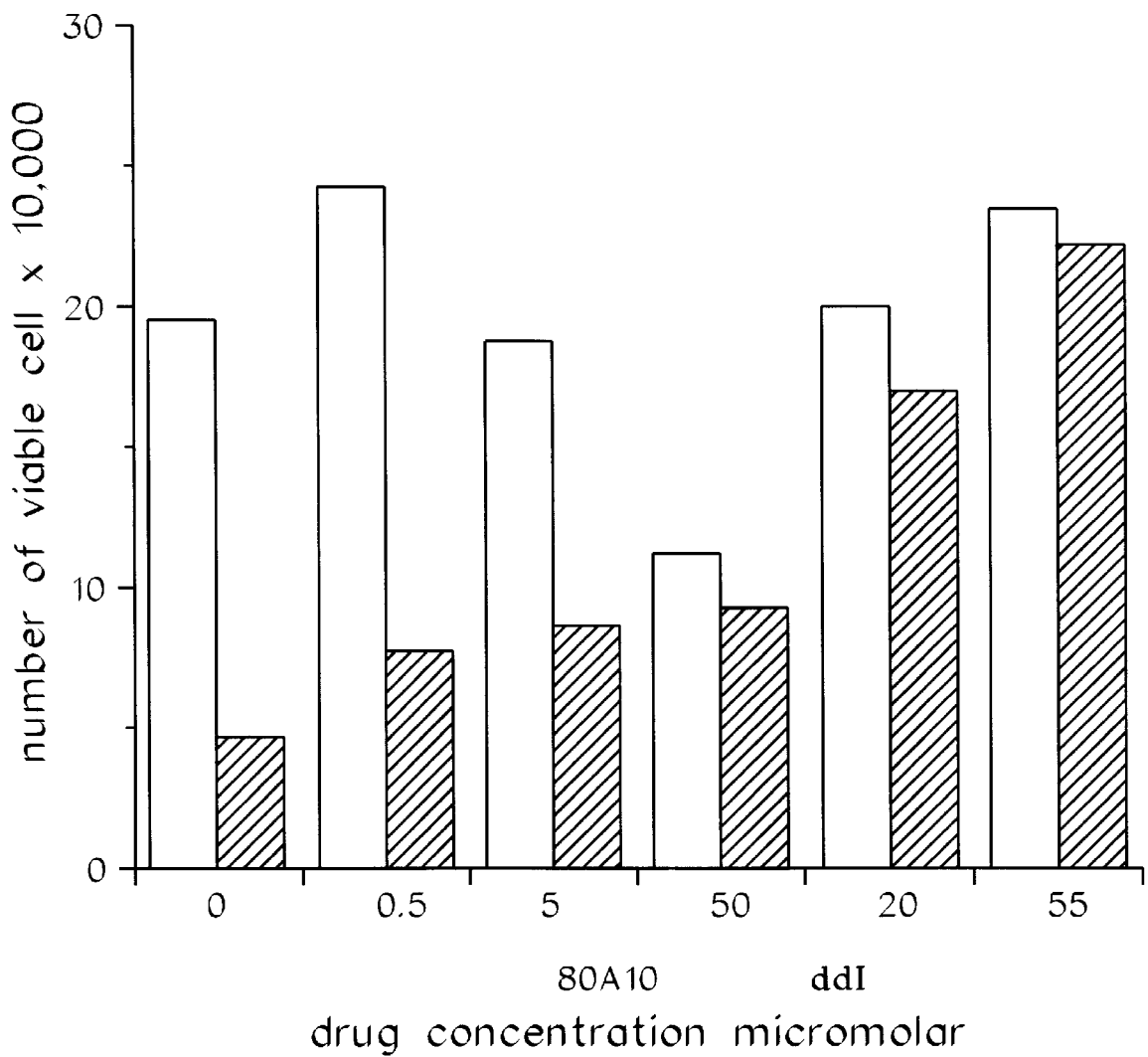
FIG. 3 shows a cytopathic effect assay using HIV 1-infected ATH8 cells. The drug concentration is indicated on the x-axis and the number of viable cells×10,000 is indicated on the y-axis. 80A10 corresponds to compound (5) and ddI is dideoxyinosine. The open bars indicate uninfected cells treated with the drug. The closed bars indicate infected cells treated with the drug.

Compounds 5–9 were evaluated against HIV-1 in immortalized OKT4$^+$ T-cells (ATH8 cells) by the cytopathic effect assay (Mitsuya and Broder, (1986) *Proc. Natl. Acad. Sci. U.S.A.*, 83: 1911). Compound 5, the adenosine derivative, was the only analogue which exhibited anti-HIV activity. A dose-dependent increase in the number of viable cells was observed from 5–50 μM, although the drug itself exhibited some toxicity in this range (FIG. 3). Since compound 5 is a racemic mixture, it is anticipated that separation of the two enantiomers will result in one responsible for toxicity and one responsible for the antiviral effect.

The synthetic approach for the 2' tert-butyl-substituted carbocyclic alcohol 10 is shown in Scheme 3 and described in Examples 16–21 below.

Synthesis of tert-Butyl-substituted Allylic Alcohol

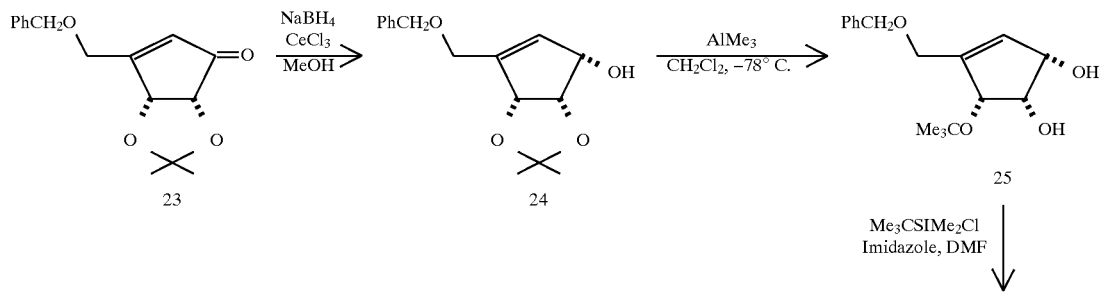

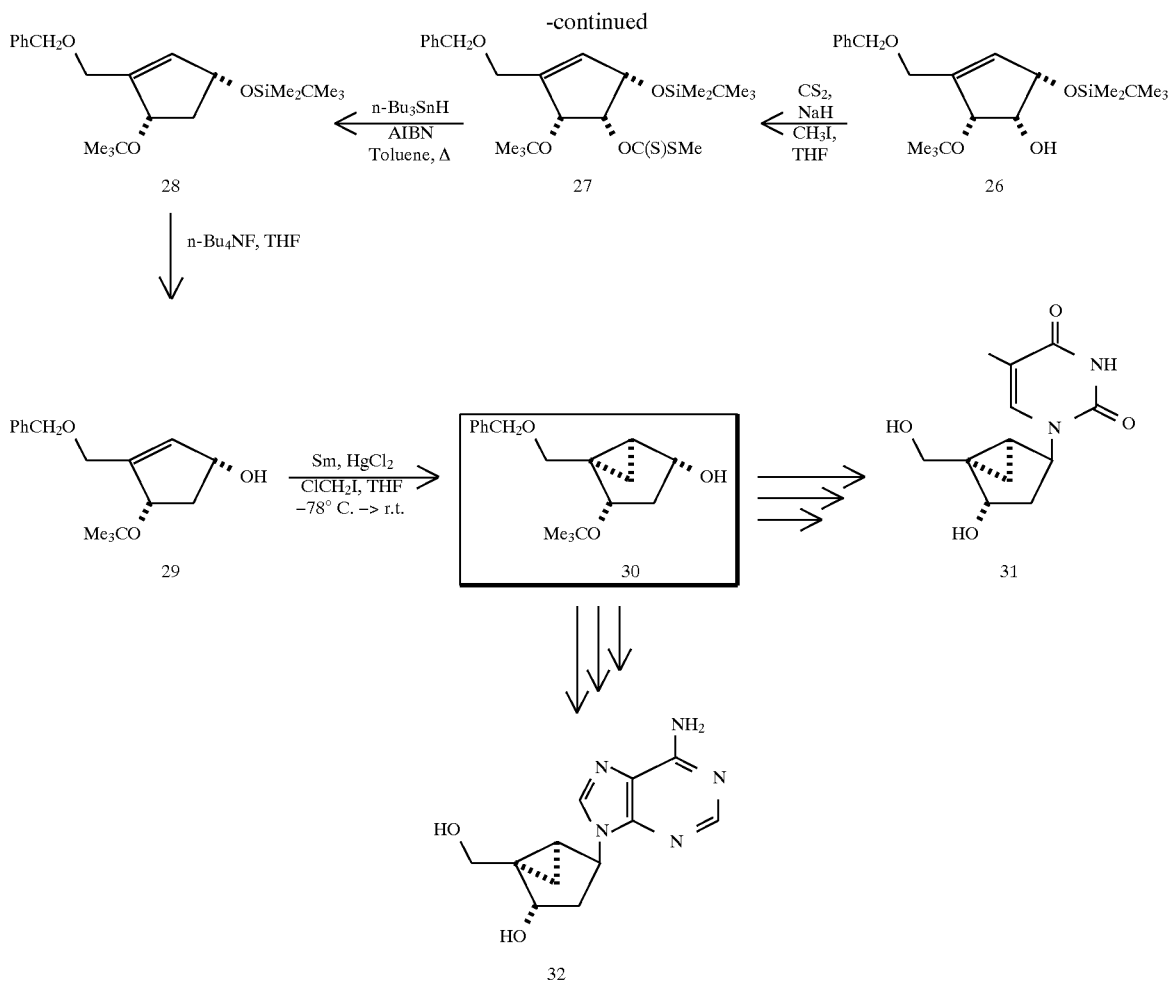

EXAMPLE 16

(1S,4R,5S)-3-[(Benzyloxy)methyl-4,5-O-isopropylidene-2-cyclopenten-1-ol 24

Compound 24 was prepared from compound 23 according to the procedure of Marquez et al., *J. Org. Chem.*, 53:5709 (1988).

EXAMPLE 17

(1S,4R,5S)-3-[(Benzyloxy)methyl]-4-tert-butyloxy-5-hydroxy-2-cyclopenten-1-ol 25

A solution of 24 (0.61 g, 2.20 mmol) was stirred in anhydrous $CH_2Cl_2$ (25 ml) at −78° C. and treated with a solution of trimethylaluminum in toluene (2M, 7.8 ml, 15.6 mmol). After the addition, the reaction was allowed to reach room temperature and stirring was continued for 18 hours. The reaction mixture was cooled again to −78° C. and quenched with an aqueous saturated solution of $NH_4Cl$ (10 ml). Since this is a very exothermic process, the addition of $NH_4Cl$ was done slowly. The mixture was filtered after reaching room temperature and the solid was washed with $CHCl_3$. The filtrate was extracted with $CHCl_3$ (3×50 ml) and the combined organic extract was washed with water (50 ml), dried ($Na_2SO_4$), and concentrated under vacuum. The crude product was purified by flash column chromatography over silica gel with a 0–50% gradient of ethyl acetate in hexane as eluent to give 0.349 g (54%) of compound 25 as a thick oil. Analysis calculated for $C_{17}H_{24}O_4$: C, 69.83; H, 8.27. Found, C, 69.57; H, 8.27.

EXAMPLE 18

(1S,4R,5S)-1-(tert-Butyldimetnylsilyloxy)-3-[(Benzoyloxy)methyl]-4-tert-butyloxy-5-hydroxy-2-cyclopentene 26

A solution of 25 (8.04 g, 27.5 mmol) and imidazole (7.05 g, 103.55 mmol) in anhydrous DMF (80 ml) was treated with tert-butyldimethylsilyl chloride 96.70 g, 44.45 mmol). The mixture was stirred at room temperature under a blanket of argon for 40 min and quenched by the addition of water (100 ml). The reaction mixture was extracted with ethyl acetate (3×100 ml), and the combined organic extract was washed with brine (2×100 ml) and dried over $Na_2SO_4$. The solvent was evaporated and the produce purified by flash column chromatography over silica gel to give 9.77 g (87.4% of pure 26 as an oil. Analysis calculated for $C_{23}H_{38}O_4Si.0.5\ H_2O$: C, 66.46; H, 9.46. Found: C, 66.41; , H, 9.31.

EXAMPLE 19

(1S,4R,5S)-1-(tert-Butyldimethylsilyloxy)-3-[(Benzyloxy)methyl]-4-tert-butyloxy-5-[(methylthio)thiocarbonyloxy-2-cyclopentene 27

A solution of 26 (9.77 g), 24.02 mmol) in anhydrous THF (100 ml) was treated with carbon disulfide (10.2 ml, 168.8 mmol). The mixture was stirred at 0° C. for 5 min, and NaH (80% suspension in oil, 2.2 g, 73.3 mmol) was added in portions. The mixture was stirred at room temperature for 30 min. Methyl iodide (19.5 ml, 313.2 mmol) was added, and after further stirring for 30 min, the reaction mixture was cooled to 0° C., and excess NaH was destroyed by the slow addition of water (very exothermic process). The organic layer was separated and the aqueous extract was dried ($Na_2SO_4$) and concentrated under vacuum. The crude product was purified by flash column chromatography over silica gel using a 0–5% gradient of ethyl acetate in hexane to give 9.83 g (82.4%) of pure 27 as an oil. Analysis calculated for $C_{25}H_{40}O_4S_2Si.0.25\ H_2O$: C, 59.90; H, 8.10; S, 12.77. Found: C, 59.84; H, 8.10; S, 12.72.

EXAMPLE 20

(1S,4R)-1-(tert-Butyldimethylsilyloxy)-3-[(Benzyloxy)methyl]-4-tert-butyl-2-cyclopentene 28

A solution of 27 (9.82 g, 19.76 mmol) and azobis (isobutyronitrile) (AIBN, 2.04 g, 12.42 mmol) in anhydrous toluene (100 ml) under a blanket of argon was heated to ca. 50° C. and treated slowly with tri-n-butyltin hydride (22 ml, 81.8 mmol). After the addition was complete, the mixture was heated (oil bath temp. 120° C.) for 1.5 hours and cooled to room temperature. The solvent was evaporated and the crude product was purified by flash column chromatography over silica gel with a gradient of 0–5% ethyl acetate in hexane to give compound 28 (5.94 g, 77%) as an oil. Analysis calculated for $C_{23}H_{38}O_3Si.0.5H_2O$: C, 69.12; H, 9.83. Found: C, 69.21; H, 9.71.

EXAMPLE 21

(1S,4R)-3-[(Benzyloxy)methyl]-4-tert-butyloxy-2-cyclopenten-1-ol 29

A solution of 28 (4.82 g, 12.36 mmol) in anhydrous THF (80 ml) was treated with a solution of tetrabutylammonium fluoride in THF (1M, 51 ml) and the resulting mixture was stirred at room temperature overnight. The solvent was evaporated and the residue treated with water and extracted with ethyl acetate (3×100 ml). The combined organic extract was washed with brine (2×100 ml) and dried ($Na_2SO_4$). The solvent was removed under reduced pressure and the crude product purified by flash column chromatography over silica gel using a gradient of 50–66% ethyl acetate in hexane to give compound 29 (3.152 g, 92%) as a clear oil. Analysis calculated for $C_{17}H_{24}O_3.0.75H_2O$: C, 70.43; H, 8.86. Found: C, 70.62; H, 8.54.

EXAMPLE 22

(1S,2S,4R,5S)-1-[(Benzoyloxy)methyl]-2-tert-butyloxy-4-hydroxybicyclo[3.1.0]hexane 30

Samarium metal (4.40 g, 29.3 mmol) was placed in a flask and dried with a flame under a stream of argon. Anhydrous THF (30 ml) and a solution of mercuric chloride (0.76 g, 2.8 mmol) in 10 ml THF were added and the mixture was stirred for 10 min prior to the addition of a solution of compound 29 (1.80 g, 6.50 mmol) in THF (30 ml). The reaction mixture was cooled to −78° C. and treated with chloroiodomethane (2.20 ml, 30 mmol). The resulting mixture was stirred continuously starting at −78° C. and allowing the temperature to reach room temperature during the course of the night. The following day, the reaction was quenched with a saturated solution of potassium carbonate (200 ml) and extracted with methylene chloride (3×100 ml). The combined organic extract was washed with brine (100 ml), dried ($Na_2SO_4$), filtered and evaporated to give nearly pure compound 30 quantitatively as a colorless oil. This product was used in the condensation steps described in the purine and pyrimidine synthetic steps described above.

Compounds 31 and 32 corresponding to the thymidine and adenosine analogs, respectively, were synthesized using compound 30 as the starting material following reaction Schemes 2 and 1, respectively, starting with the step following cyclopropanation.

(1R,2S,4S,5S)-1-Hydroxymethyl-4-(5-methyl-2,4(1,3H)-dioxopyrimidin-1-yl)bicyclo [3.1.0]hexane 31

The thymidine analog 31 was obtained as a white crystalline product having the following parameters: melting point=239°–241° C. $[\alpha]_D25$=+47.14; FAB MS m/z (relative intensity) 253 (MH+, 100), 127 (b+2H, 40). Analysis calculated for $C_{12}H_{16}O_4N_2.0.33H_2O$: C, 55.81; H, 6.50; N, 10.85. Found: C, 55.91; H, 6.51; N, 10.73.

(1R,2S,4S,5S)-1-Hydroxymethyl-4-(6-amino-9-purinyl) bicyclo[3.1.0]hexane 32

The adenosine analog 32 was obtained as a white solid, melting point 259°–261° C.; FAB MS m/z (relative intensity) 262 (MH+, 100), 136 (b+2H, 58).

In the final step of the purine synthetic scheme (Scheme 1), and in the thymidine/uracil synthetic step of the pyrimidine synthetic scheme (Scheme 2), the benzyl protecting groups removed by cleavage with $BCl_3$. This same treatment removes the tert-butyl group at the 2' position when compound 30 is used as the starting material for synthesis of the nucleoside analogs, thus leaving a 2'-OH group.

The description above is illustrative and not restrictive. Accordingly, many variations of the invention will be apparent to one skilled in the art on review of this disclosure, and the invention can be embodied in these various specific forms without departing from it in spirit or essential characteristics. For example, it should be apparent from the foregoing that various purine and pyrimidine analogues can be substituted in the Examples to achieve similar results. The scope of the invention is therefore indicated by the appended claims rather than by the foregoing description.

What is claimed is:

1. A nucleoside analogue of the formula

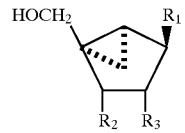

wherein $R_1$ is selected from the group consisting of adenine-9-yl, guanine-9-yl, thymine-1-yl, uracil-1-yl, cytosine-1-yl, and $R_2$ and $R_3$ are independently H or OH.

2. A nucleoside analogue according to claim 1, wherein $R_1$ is guanine-9-yl or adenine-9-yl, and $R_2$=$R_3$=OH.

3. The compound of claim 1 wherein $R_2$=$R_3$=H.

4. The compound of claim 1 wherein $R_2$=OH, $R_3$=H.

5. The compound of claim 1 wherein $R_2$=$R_3$=OH.

6. A nucleoside analogue according to claim 1, wherein $R_1$ is guanine-9-yl or adenine-9-yl, and $R_2$=$R_3$=H.

7. A nucleoside analogue according to claim 1, wherein $R_1$ is cytosine-1-yl, uracil-1-yl, or thymine-1-yl, and $R_2$=$R_3$=H.

8. A nucleoside analogue of the formula

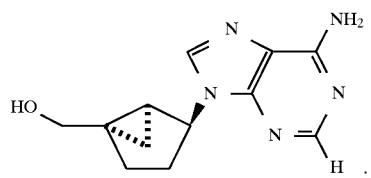

9. A nucleoside analogue of the formula

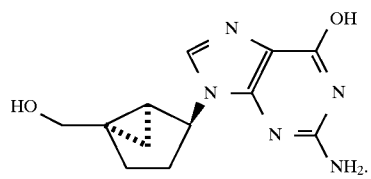

10. A nucleoside analogue of the formula

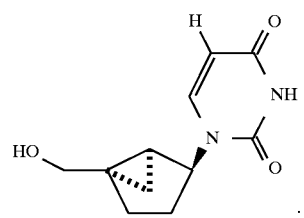

11. A nucleoside analogue of the formula

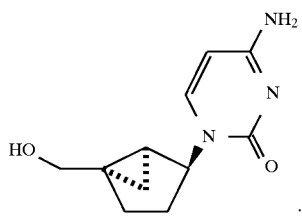

12. A nucleoside analogue of the formula

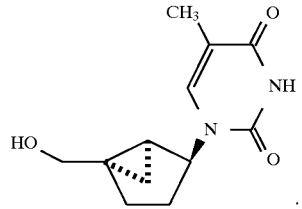

13. A nucleoside analogue according to claim 1, wherein $R_1$ is guanine-9-yl or adenine-9-yl, $R_2$=OH and $R_3$=H.

14. A nucleoside analogue according to claim 1, wherein $R_1$ is cytosine-1-yl, uracil-1-yl, or thymine-1-yl, $R_2$=OH and $R_3$=H.

15. A nucleoside analogue according to claim 1, wherein R1 is adenin-9-yl or guanin-9-yl.

16. A nucleoside analogue according to claim 1, wherein $R_1$ is cytosine-1-yl, thymine-1-yl, or uracil-1-yl, and $R_2$=$R_3$=OH.

* * * * *